US012110267B2

(12) United States Patent
Miller et al.

(10) Patent No.: US 12,110,267 B2
(45) Date of Patent: Oct. 8, 2024

(54) METHODS FOR VICINAL DIOL SEPARATION

(71) Applicant: BOARD OF TRUSTEES OF MICHIGAN STATE UNIVERSITY, East Lansing, MI (US)

(72) Inventors: Dennis J. Miller, Okemos, MI (US); Carl T. Lira, East Lansing, MI (US); Lars Peereboom, Haslett, MI (US); Scott F. Parker, Fowlerville, MI (US); Thomas D. Dionise, Lansing, MI (US); William G. Killian, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 672 days.

(21) Appl. No.: 17/283,090

(22) PCT Filed: Oct. 7, 2019

(86) PCT No.: PCT/US2019/054998
§ 371 (c)(1),
(2) Date: Apr. 6, 2021

(87) PCT Pub. No.: WO2020/076699
PCT Pub. Date: Apr. 16, 2020

(65) Prior Publication Data
US 2021/0340088 A1 Nov. 4, 2021

Related U.S. Application Data

(60) Provisional application No. 62/742,642, filed on Oct. 8, 2018.

(51) Int. Cl.
*C07C 29/92* (2006.01)
*B01J 19/00* (2006.01)
(Continued)

(52) U.S. Cl.
CPC .......... *C07C 29/92* (2013.01); *B01J 19/0066* (2013.01); *B01J 19/1862* (2013.01);
(Continued)

(58) Field of Classification Search
CPC ....... C07C 29/92; C07C 29/95; C07C 31/202; C07C 31/205; C07C 31/207; C07C 29/88
See application file for complete search history.

(56) References Cited

U.S. PATENT DOCUMENTS 4,935,102 A 6/1990 Berg
6,548,681 B1 4/2003 Chopade et al.
(Continued)

OTHER PUBLICATIONS

International Application No. PCT/US19/54998, International Search Report and Written Opinion, mailed Jan. 2, 2020.

*Primary Examiner* — Yate' K Cutliff
(74) *Attorney, Agent, or Firm* — MARSHALL, GERSTEIN & BORUN LLP

(57) ABSTRACT

The disclosure relates to methods for separating mixtures of polyols, in particular mixtures of two of more different vicinal diols having close boiling points, thus making them difficult or impossible to separate using conventional distillation techniques. The polyol mixture is reacted with an aldehyde or ketone acetalization agent to form one or more acetals as corresponding acetalization reaction products. The acetalization reaction products are more easily separable either from each other (such as via distillation) or from an unreacted vicinal diol (such as via extraction, settling, or other phase separation). After separation, hydrolysis is performed on the acetalization reaction products to recover the vicinal diols as separate, purified components. The methods provide cost-effective processes for separating different polyols originally formed in admixture.

23 Claims, 5 Drawing Sheets

III. Selective Acetal Formation via Product Addition

(51) Int. Cl.
*B01J 19/18* (2006.01)
*C07C 29/09* (2006.01)
*C07C 29/88* (2006.01)
*C07C 31/20* (2006.01)

(52) U.S. Cl.
CPC ............ C07C 29/095 (2013.01); C07C 29/88 (2013.01); C07C 31/202 (2013.01); C07C 31/205 (2013.01); C07C 31/207 (2013.01)

(56) References Cited

U.S. PATENT DOCUMENTS

| | | |
|---|---|---|
| 8,604,223 B2 | 12/2013 | Selifonov et al. |
| 2003/0187281 A1* | 10/2003 | Miller ................... C07C 29/095 |
| | | 549/430 |
| 2017/0327446 A1* | 11/2017 | Zhang .................... C07C 31/18 |

* cited by examiner

Physical Properties of Aldehydes, Ketones, Polyols, and Acetals

| Compound | Boiling Point | Solubility in Water | Density |
|---|---|---|---|
| Methanal (formaldehyde) | -19°C | 400 g/l | 0.815 g/ml |
| Ethanal (acetaldehyde) | 20°C | miscible | 0.784 g/ml |
| Propanal | 46°C | 20 g/100 ml (20°C) | 0.810 g/ml |
| Butanal (butyraldehyde) | 75°C | 7.6 g/100 ml (20°C) | 0.802 g/ml |
| Pentanal | 102°C | very slight | 0.810 g/ml |
| 2-Methylpropanal (isobutyraldehyde) | 63°C | moderate | 0.79 g/ml |
| 2-Propanone (acetone) | 56°C | miscible | 0.785 g/ml |
| 2-Buatanone (MEK) | 80°C | 27.5 g/100 ml (20°C) | 0.805 g/ml |
| 2-Pentanone | 102°C | 6% (20°C) | 0.81 g/ml |
| 3-Pentanone | 102°C | 3.5 g/100 ml | 0.81 g/ml |
| 1,2-Ethanediol (EG) | 197.3°C | miscible | 1.11 g/ml |
| 1,2-Propanediol (PG) | 188.2°C | miscible | 1.04 g/ml |
| 1,3-Propanediol | 211-217°C | miscible | 1.06 g/ml |
| 1,2-Butanediol (BDO) | 195-196.9°C | miscible | 1.00 g/ml |
| 2,3-Butanediol | 177°C | miscible | 0.99 g/ml |
| 1,3-Butanediol | 204-210°C | 1000 g/l | 1.01 g/ml |
| 2-Propyl-1,3-dioxolane (PD) | 131°C | (low) | |
| 4-Ethyl-2-propyl-1,3-dioxolane (EPD) | 158°C | (low) | |

FIGURE 5

METHODS FOR VICINAL DIOL SEPARATION

CROSS REFERENCE TO RELATED APPLICATION

This application is a National Stage application of International Application No. PCT/US2019/054998, filed Oct. 7, 2019, which claims priority to U.S. Provisional Application No. 62/742,642, (filed Oct. 8, 2018), both of which are incorporated herein by reference in their entireties.

STATEMENT OF GOVERNMENT INTEREST

None.

BACKGROUND OF THE DISCLOSURE

Field of the Disclosure

The disclosure relates to methods for separating polyols, in particular mixtures of two of more different vicinal diols having close boiling points. The polyol mixture is reacted with an aldehyde or ketone acetalization agent to form one or more corresponding acetal reaction products which are more easily separable, after which hydrolysis is performed to recover the vicinal diols as separate, purified components.

Brief Description of Related Technology

Chemical mixtures of similar compounds lead to a complex separation problem. An example of this is the separation of vicinal diols, where diols in such mixtures can have boiling points within 0.5° C. of one another, and therefore distillation cannot be used for adequate separation. Mixtures of vicinal diols are commonly made by hydrogenolysis of carbohydrate sugar alcohols. Interest in this field has returned with interest in creation of commercially viable polyester precursors using natural materials, which requires that the polyols be separated to high purity. There is an absence of cost-effective methods for separating the resulting mixture of polyols into it individual polyol components.

Chopade et al. U.S. Pat. No. 6,548,681 is directed to process for the recovery of a polyol from an aqueous solution, in particular for the separation of a polyol or multiple polyols in admixture with other organic compounds, usually those produced with the polyol. The process uses a reactive distillation column to form a cyclic acetal or ketal in a reaction mixture of the polyol and an aldehyde or ketone. The polyols can include ethylene glycol and propylene glycol.

SUMMARY

In a first aspect, the disclosure relates to a method for separating polyols, the method comprising: feeding to a reactor: (i) a first polyol reactant having 2 to 10 carbon atoms and comprising at least two hydroxyl groups on adjacent carbon atoms, (ii) a second polyol reactant different from the first polyol reactant, having 2 to 10 carbon atoms, and comprising at least two hydroxyl groups on adjacent carbon atoms, (iii) an acetalization reactant comprising at least one of an aldehyde having 1 to 10 or 3 to 10 carbon atoms and a ketone having 3 to 10 or 4 to 10 carbon atoms, and (iv) (optionally) water; forming in the reactor via an acid-catalyzed reaction: (i) a first acetalization product comprising a reaction product between the first polyol reactant and the acetalization reactant, (ii) a second acetalization product comprising a reaction product between the second polyol reactant and the acetalization reactant, and (iii) water; separating a reactor product mixture comprising the first acetalization product, the second acetalization product, and the water into (i) a water-immiscible product comprising the first acetalization product and the second acetalization product, and (ii) an aqueous product comprising the water; separating the water-immiscible product into (i) a first product comprising the first acetalization product, and (ii) a second product comprising the second acetalization product; hydrolyzing the first product to form the first polyol reactant from the first acetalization product; and hydrolyzing the second product to form the second polyol reactant from the second acetalization product. In an embodiment, the method can further comprise: recycling at least a portion of the aqueous product as a water feed to one or more of (i) the reactor, (ii) a first hydrolysis apparatus for hydrolyzing the first product, and (iii) a second hydrolysis apparatus for hydrolyzing the second product.

In a second aspect, the disclosure relates to a method for separating polyols, the method comprising: feeding to a reactor comprising a reactive distillation column: (i) a first polyol reactant having 2 to 10 carbon atoms and comprising at least two hydroxyl groups on adjacent carbon atoms, (ii) a second polyol reactant different from the first polyol reactant, having 2 to 10 carbon atoms, and comprising at least two hydroxyl groups on adjacent carbon atoms, (iii) an acetalization reactant comprising at least one of an aldehyde having 1 to 10 or 3 to 10 carbon atoms and a ketone having 3 to 10 or 4 to 10 carbon atoms, and (iv) water; forming in the reactor via an acid-catalyzed reaction: (i) a first acetalization product comprising a reaction product between the first polyol reactant and the acetalization reactant, (ii) a second acetalization product comprising a reaction product between the second polyol reactant and the acetalization reactant, and (iii) water; hydrolyzing in the reactor via an acid-catalyzed reaction the second acetalization product to re-form the second polyol reactant from the second acetalization product; removing from the reactor (i) a first product comprising the first acetalization product, and (ii) a second product comprising the re-formed second polyol reactant; and hydrolyzing the first product to form the first polyol reactant from the first acetalization product.

In a third aspect, the disclosure relates to a method for separating polyols, the method comprising: feeding to a reactor: (i) a first polyol reactant having 2 to 10 carbon atoms and comprising at least two hydroxyl groups on adjacent carbon atoms, (ii) a second polyol reactant different from the first polyol reactant, having 2 to 10 carbon atoms, and comprising at least two hydroxyl groups on adjacent carbon atoms, (iii) an acetalization reactant comprising at least one of an aldehyde having 1 to 10 or 3 to 10 carbon atoms and a ketone having 3 to 10 or 4 to 10 carbon atoms, (iv) a first acetalization product comprising a reaction product between the first polyol reactant and the acetalization reactant, and (v) (optionally) water; forming in the reactor via an acid-catalyzed reaction: (i) (optionally) further first acetalization product comprising a reaction product between the first polyol reactant and the acetalization reactant, (ii) a second acetalization product comprising a reaction product between the second polyol reactant and the acetalization reactant, and (iii) water; separating a reactor product mixture comprising the first acetalization product, the second acetalization product, the first polyol reactant, and the water into (i) a water-immiscible product comprising the first acetalization product and the second acetalization product, and (ii)

an aqueous product comprising the first polyol reactant and the water; separating the water-immiscible product into (i) a first product comprising the first acetalization product, and (ii) a second product comprising the second acetalization product; and hydrolyzing the second product to form the second polyol reactant from the second acetalization product. In an embodiment, the method can further comprise: recycling the first product comprising the first acetalization product to the reactor. In an embodiment, the method can further comprise: feeding to a second reactor: (i) the first product comprising the first acetalization product, (ii) the acetalization reactant, and (iii) the aqueous product comprising the first polyol reactant and the water; forming in the second reactor via an acid-catalyzed reaction: (i) (optionally) the first acetalization product comprising a reaction product between the first polyol reactant and the acetalization reactant, and (ii) the second acetalization product comprising a reaction product between the second polyol reactant and the acetalization reactant; separating a second reactor product mixture comprising the first polyol, the second acetalization product, the acetalization reactant, and the water into (i) a second water-immiscible product comprising the second acetalization product and the acetalization reactant, and (ii) a second aqueous product comprising the water; and feeding the second water-immiscible product to the reactor.

In a fourth aspect, the disclosure relates to a method for separating polyols, the method comprising: feeding to a reactor comprising a reactive extraction vessel): (i) a first polyol reactant having 2 to 10 carbon atoms and comprising at least two hydroxyl groups on adjacent carbon atoms, (ii) a second polyol reactant different from the first polyol reactant, having 2 to 10 carbon atoms, and comprising at least two hydroxyl groups on adjacent carbon atoms, (iii) an acetalization reactant comprising at least one of an aldehyde having 1 to 10 or 3 to 10 carbon atoms and a ketone having 3 to 10 or 4 to 10 carbon atoms, and (iv) water; forming in the reactor via an acid-catalyzed reaction: (i) (optionally) a first acetalization product comprising a reaction product between the first polyol reactant and the acetalization reactant, (ii) a second acetalization product comprising a reaction product between the second polyol reactant and the acetalization reactant, and (iii) water; removing from the reactor (i) a first product comprising the first polyol reactant and the water, and (ii) a second product comprising the second acetalization product and the acetalization reactant; and hydrolyzing the second product to form the second polyol reactant from the second acetalization product.

Various refinements of the disclosed methods are possible.

In a refinement, the first polyol reactant and the second polyol reactant are independently selected from the group consisting of saturated or unsaturated linear hydrocarbon polyols, branched hydrocarbon polyols, and cyclic hydrocarbon polyols. The first polyol reactant and the second polyol reactant are generally provided in admixture as a feed to the reactor, for example with a first polyol concentration in a range from 5 wt. % to 95 wt. % (e.g., at least 5, 10, 15, 20, 30, 40, 50, 60, or 70 wt. % and/or up to 20, 30, 40, 50, 60, 70, 80, 85, 90, or 95 wt. %) and with a second polyol concentration in a range from 5 wt. % to 95 wt. % (e.g., at least 5, 10, 15, 20, 30, 40, 50, 60, or 70 wt. % and/or up to 20, 30, 40, 50, 60, 70, 80, 85, 90, or 95 wt. %). The feed stream with the first and second polyols can include other polyols for separation (e.g., third, fourth, etc. polyol reactants), acetalization reactant (e.g., when combined with the polyols upstream of the reactor instead of being introduced separately into the reactor), and/or water. Suitably, the feed stream contains not more than 10 wt. % (e.g., up to 0.1, 1, 2, 5, or 10 wt. %) of components other than the polyol reactants and optionally the acetalization reactant and/or water.

In a refinement, the first polyol reactant and the second polyol reactant each have only two hydroxyl groups. In other refinements, one or both of the first polyol reactant and the second polyol reactant can have more than two hydroxyl groups, but each still having a vicinal hydroxyl group pair for acetalization. In some alternative embodiments, one or both of the first polyol reactant and the second polyol reactant can have two hydroxyl groups on non-adjacent carbons, but which can still react to form cyclic acetal compounds (e.g., two hydroxyl groups on separate carbon atoms with one intervening carbon atom having no hydroxyl groups). For example, a mixture of 1,3-propanediol (BP 211-217° C.) and 1,3-butanediol (BP 204-210° C.) can form corresponding acetals between the 1,3 carbons of each polyol (or more generally between the (n) and (n+2) carbons in a polyol having hydroxyl groups thereon).

In a refinement, the first polyol reactant is 1,2-ethanediol (ethylene glycol), and the second polyol reactant is 1,2-propanediol (propylene glycol).

In a refinement, the first polyol reactant is 1,2-ethanediol (ethylene glycol), and the second polyol reactant is 1,2-butanediol.

In a refinement, the first polyol reactant and the second polyol reactant are independently selected from the group consisting of 1,2-ethanediol (ethylene glycol), 1,2-propanediol (propylene glycol), 1,2-butanediol, 1,2-butanediol, 2,3-butanediol, 1,2-pentanediol, 2,3-pentanediol, 1,2-hexanediol, 2,3-hexanediol, 3,4-hexanediol, 1,2-heptanediol, 1,2-octanediol, 1,2-nonanediol, and 1,2-decanediol.

In a refinement, the first polyol reactant and the second polyol reactant have boiling points that are within 10° C. or 15° C. of each other (e.g., different by at least 0.2, 0.5 or 1° C. and/or up to 0.5, 1, 2, 5, 10, or 15° C.). For example, ethylene glycol has a BP of about 197° C., and propylene glycol has a BP of about 188° C., for a difference of about 9° C. Similarly, ethylene glycol has a BP of about 197° C., and 1,2-butanediol has a BP of about 196° C., for a difference of about 1° C.). The methods disclosed herein are generally advantageous when the two boiling points are within 15° C. of each other and/or when the relative volatilities are about 1.2 or less (e.g., a volatility ratio between 1 and 1.1 or 1.2 for the more volatile compound relative to the less volatile compound). Comparatively increased capital and/or energy costs for the disclosed method can be nonetheless more efficient than a conventional distillation column based on separation efficiencies not otherwise attainable with a conventional distillation column alone.

In a further refinement, the first acetalization product and the second acetalization product have boiling points that are more than 5° C. or 10° C. apart from each other (e.g., different by at least 5, 10, 15, 20, or 25° C. and/or up to 20, 30, 40, 50, or 100° C. difference). For example, 2-propyl-1,3-dioxolane (PD) has a BP of about 131° C. and 4-ethyl-2-propyl-1,3-dioxolane (EPD) has a BP of about 158° C. for a difference of about 27° C. Suitably one or both of the first acetalization and second acetalization products have boiling points above that of water. In some cases, such as the method illustrated in the fourth aspect of the disclosure, the method utilizes extraction instead of distillation for separation, so the first and second acetalization products can have any boiling point difference.

In a refinement, the acetalization reactant is selected from the group consisting of saturated or unsaturated linear hydrocarbon aldehydes or ketones, branched hydrocarbon aldehydes or ketones, and cyclic hydrocarbon ketones. Many aldehydes or ketones can be suitable for the separation in terms of the corresponding acetals, but ketones are generally slower to react than aldehydes and may be less thermodynamically favorable to form product. As used herein, the terms "acetal" and "acetalization product" have the general structure $R^1R^2C(OR^3)(OR^4)$, where $R^2$, $R^3$, and $R^4$ are groups other than hydrogen (H), and $R^1$ can be hydrogen (H) or a group other than hydrogen (H). In reactions according to the disclosure, the $R^3$ and $R^4$ groups have a reaction product structure corresponding to the polyol reactant, and the $R^1$ and $R^2$ groups have a reaction product structure corresponding to the acetalization reactant. Accordingly, acetals and acetalization products according to the disclosure generally have a cyclic diether base structure. Thus, the terms "acetalization" and "acetalization product" are used generically encompass both (i) reaction of a polyol with an aldehyde to form a corresponding acetal with $R^1$ as hydrogen and $R^2$, $R^3$, and $R^4$ as other than hydrogen (e.g., denoted by $HR^2C(OR^3)(OR^4)$), and (ii) reaction of a polyol with a ketone to form a corresponding acetal with $R^1$, $R^2$, $R^3$, and $R^4$ as other than hydrogen (e.g., denoted by $R^1R^2C(OR^3)(OR^4)$), which can equivalently be considered a ketal or ketalization product as a subset or type of acetal or acetalization product. Likewise, the acetalization reactant generically includes both aldehydes and ketones as described above, where a ketone acetalization reactant can be equivalently be considered a ketalization reactant as a subset or type of acetalization reactant.

The acetalization reactant generally includes at least one of an aldehyde having 1 to 10 or 3 to 10 carbon atoms (e.g., at least 1, 2, 3, 4, or 5 and/or up to 5, 6, 8 or 10 carbon atoms) and a ketone having 3 to 10 or 4 to 10 carbon atoms (e.g., at least 3, 4, 5, or 6 and/or up to 6, 8 or 10 carbon atoms). In a refinement, the acetalization reactant is selected from the group consisting of propanal (propionaldehyde), butanal (butyraldehyde), 2-methylpropanal (isobutyraldehyde), pentanal, hexanal, heptanal, octanal, nonanal, decanal, 2-buatanone, 2-pentanone, 3-pentanone, 2-hexanone, 3-hexanone, 2-heptanone, 2-octanone, 2-nonanone, 2-decanone. In some embodiments, the acetalization reactant can further include aldehydes having 1 or 2 carbon atoms (e.g., methanal (formaldehyde), ethanal (acetaldehyde)), and/or the acetalization reactant can further include ketones having 3 carbon atoms (e.g., 2-propanone (acetone)).

In a refinement, the acetalization reactant comprises butanal (butyraldehyde).

In a refinement, the acetalization reactant has a solubility in water of up to 30 g/100 ml (e.g., at least 0.01, 0.1, or 1 g/100 ml water and/or up to 5, 10, 15, 20, 25, or 30 g/100 ml water, such as measured at 20° C.). Suitably, the acetalization reactant has a density of at least 0.7, 75, or 0.8 g/ml and up to 0.85, 0.9, or 0.95 g/ml to facilitate phase separation/more rapid settling times between an organic phase and an aqueous phase.

In a refinement, the first acetalization product and the second acetalization product have a solubility in water of up to 30 g/100 ml (e.g., at least 0.01, 0.1, or 1 g/100 ml water and/or up to 5, 10, 15, 20, 25, or 30 g/100 ml water, such as measured at 20° C.). In contrast, the corresponding first and second polyol reactants have higher water solubilities, for example being miscible or essentially completely soluble in water.

In a refinement, the method further comprises feeding to the reactor a feed stream comprising the first polyol reactant and the second polyol reactant, wherein the feed stream is substantially free of components other than polyol reactants and acetalization reactants. The feed stream can include other polyols (e.g., vicinal diols or other polyols capable of acetalization) and/or the acetalization reactant in addition to the first and second polyol reactants. The feed stream suitably does not include more than 10, 5, 2, 1, or 0.1 wt. % of other non-polyol/non-acetalization components (e.g., water or otherwise), relative to the feed stream components. Other streams including water and/or acetalization products can be fed to the reactor as separate streams where they mix in the reactor. In some embodiments, one or more feed streams could include possible byproducts from an upstream process forming the first and second polyols (e.g., a sugar/sugar alcohol hydrogenolysis process for ethylene glycol/propylene glycol production). Example byproducts can include one or more of glycerol, unreacted C5/C6 sugar alcohols, C4/C5 polyols, and lactic acid, which suitably are collectively and/or individually present at not more than 10, 5, 2, 1, or 0.1 wt. % relative to the feed stream components. In some embodiments, the feed streams are free or substantially free from such byproducts (e.g., less than 0.1 or 0.01 wt. % in feed).

In a refinement, the reactor comprises a heterogeneous solid-phase acid catalyst therein for forming at least one of the first acetalization product and the second acetalization product, depending whether one or both acetalization products are formed in the reactor. Many suitable solid acid catalysts are commercially available. Examples of such heterogeneous solid-phase acid catalysts include an AMBERLYST, NAFION, or other acidic ion-exchange resin, for example based on a sulfonated polystyrene, a sulfonated tetrafluoroethylene.

In a refinement, the method further comprises feeding to the reactor a homogeneous acid catalyst (e.g., sulfuric acid, p-toluene sulfonic acid (PTSA)) for forming at least one of the first acetalization product and the second acetalization product, depending whether one or both acetalization products are formed in the reactor.

In a refinement, the method further comprises, after forming in the reactor at least one of the first acetalization product and the second acetalization product: separating a product stream comprising the first polyol reactant and water into (i) a purified first polyol product (e.g., at least 90, 95, 98, or 99 wt. % first polyol) and (ii) water. This separation can be performed in a distillation column, such as with the purified first polyol product as the bottoms and the water as the distillate. This separation can be performed after a hydrolysis step (such as in FIG. 1 or 2), after a liquid/liquid separation step (such as in FIG. 3), or after a liquid/liquid (reactive) extraction step (such as in FIG. 4).

In a refinement, the method further comprises, after forming in the reactor at least one of the first acetalization product and the second acetalization product: separating a product stream comprising the second polyol reactant and water into (i) a purified second polyol product (e.g., at least 90, 95, 98, or 99 wt. % second polyol) and (ii) water. This separation can be performed in a distillation column, such as with the purified second polyol product as the bottoms and the water as the distillate. This separation can be performed after a hydrolysis step (such as in FIG. 1, 3, or 4) or after a reactive distillation step with in situ hydrolysis (such as in FIG. 2).

While the disclosed methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein:

FIG. 5 includes a table listing boiling point, water solubility, and density properties for various aldehydes, ketones, polyols, and acetals that can be used as various reactants or products in the disclosed methods.

DETAILED DESCRIPTION

The disclosure relates to methods for separating mixtures of polyols, in particular mixtures of two of more different vicinal diols having close boiling points, thus making them difficult or impossible to separate using conventional distillation techniques. The polyol mixture is reacted with an aldehyde or ketone acetalization agent to form one or more cyclic acetals as corresponding acetalization reaction products. In cyclic acetals, the oxygen atoms are now within the cyclic structure of the compounds. The acetals, unlike the vicinal diols, have widely separated boiling points that are easier to separate with distillation. Alternatively, selective reaction of acetalization agent with a particular vicinal diol allows efficient separation of one diol from another through phase partitioning. Thus, the acetalization reaction products are more easily separable either from each other (such as via distillation) or from an unreacted vicinal diol (such as via extraction, settling, or other phase separation). After separation, hydrolysis is performed on the acetalization reaction products to recover the vicinal diols as separate, purified components. The methods provide cost-effective processes for separating different polyols originally formed in admixture.

Figure 1:
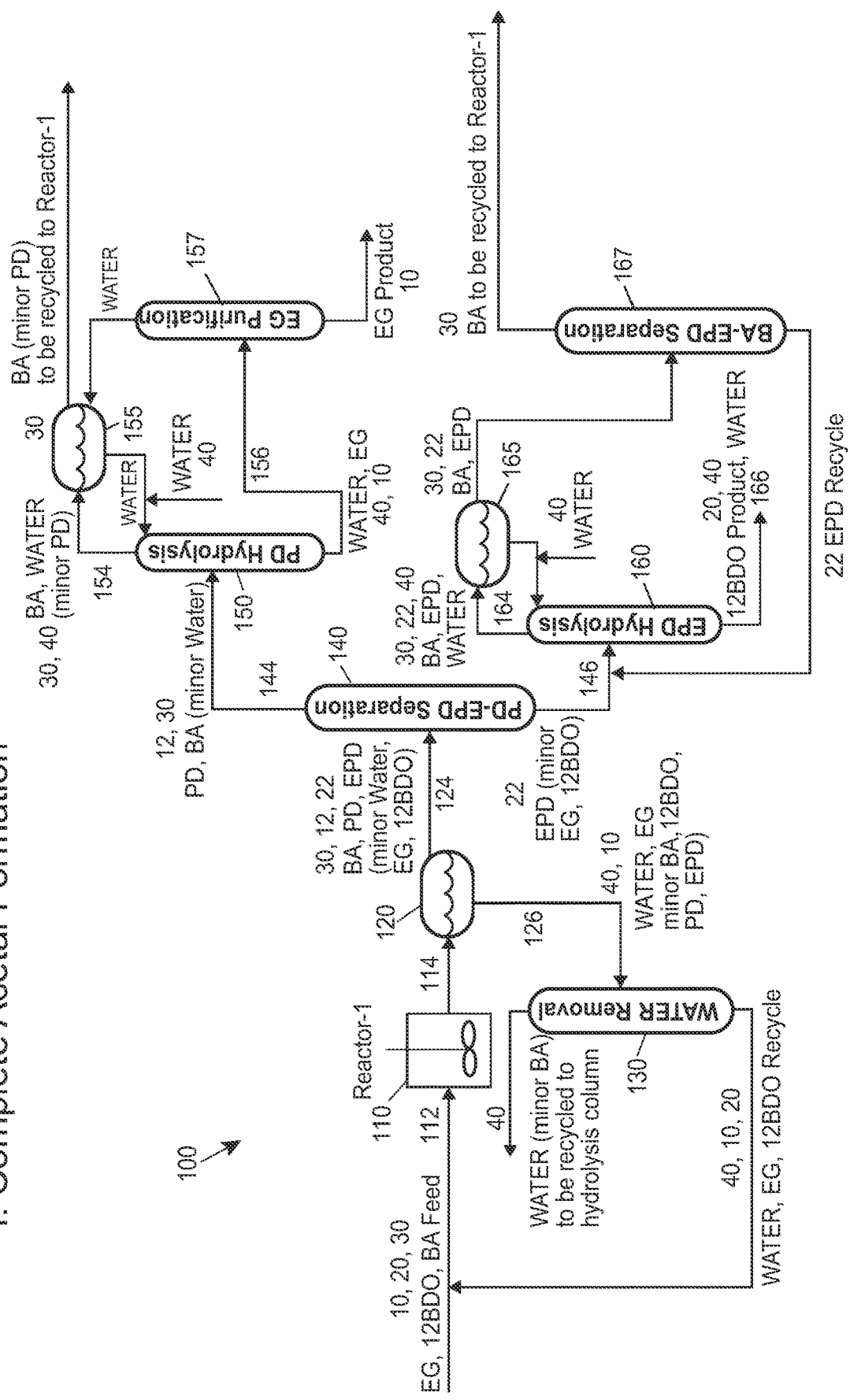
FIG. 1 is a process flow diagram illustrating a method for separating polyols according to a first aspect of the disclosure.
Figure 2:
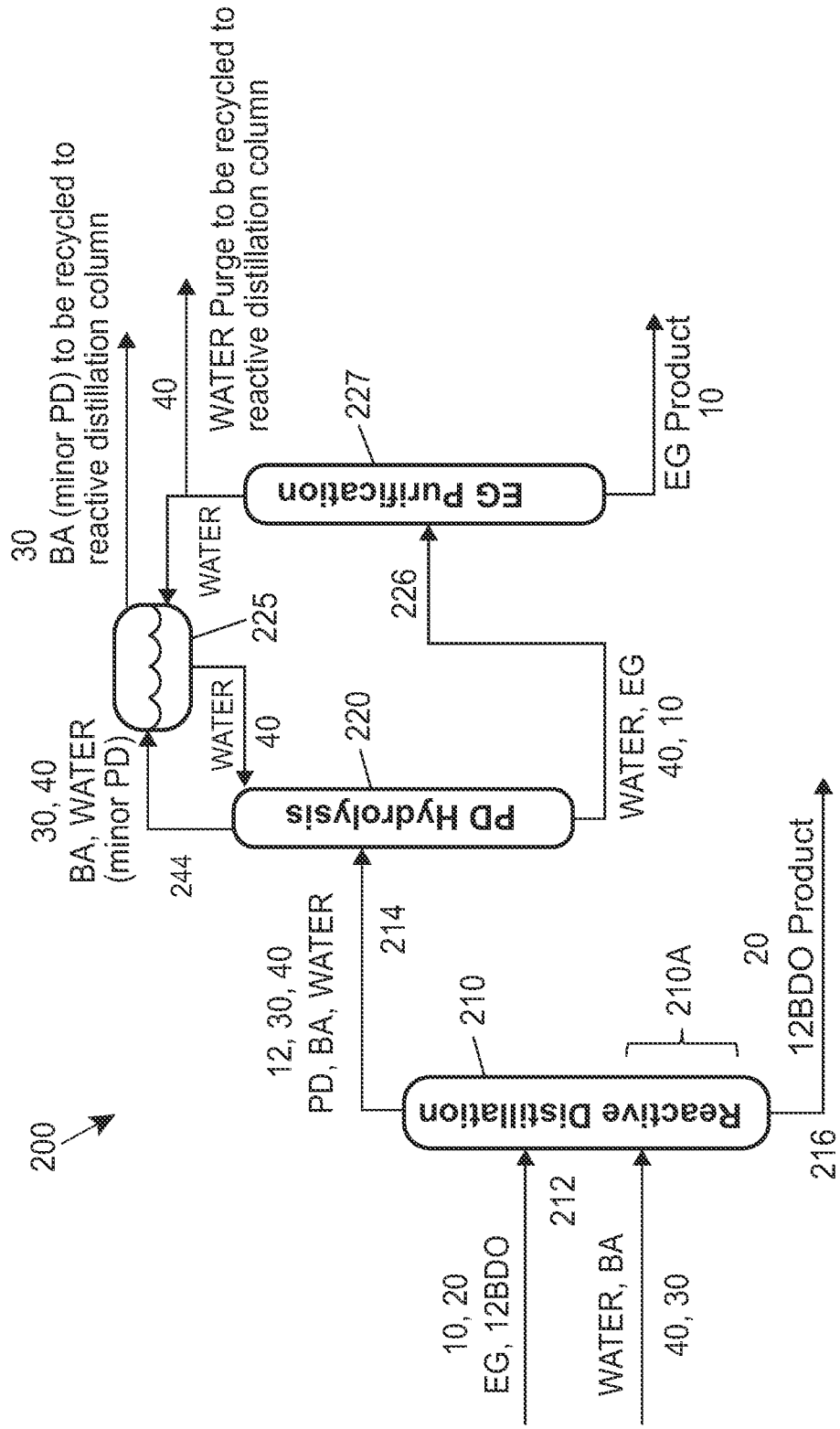
FIG. 2 is a process flow diagram illustrating a method for separating polyols according to a second aspect of the disclosure.
Figure 3:
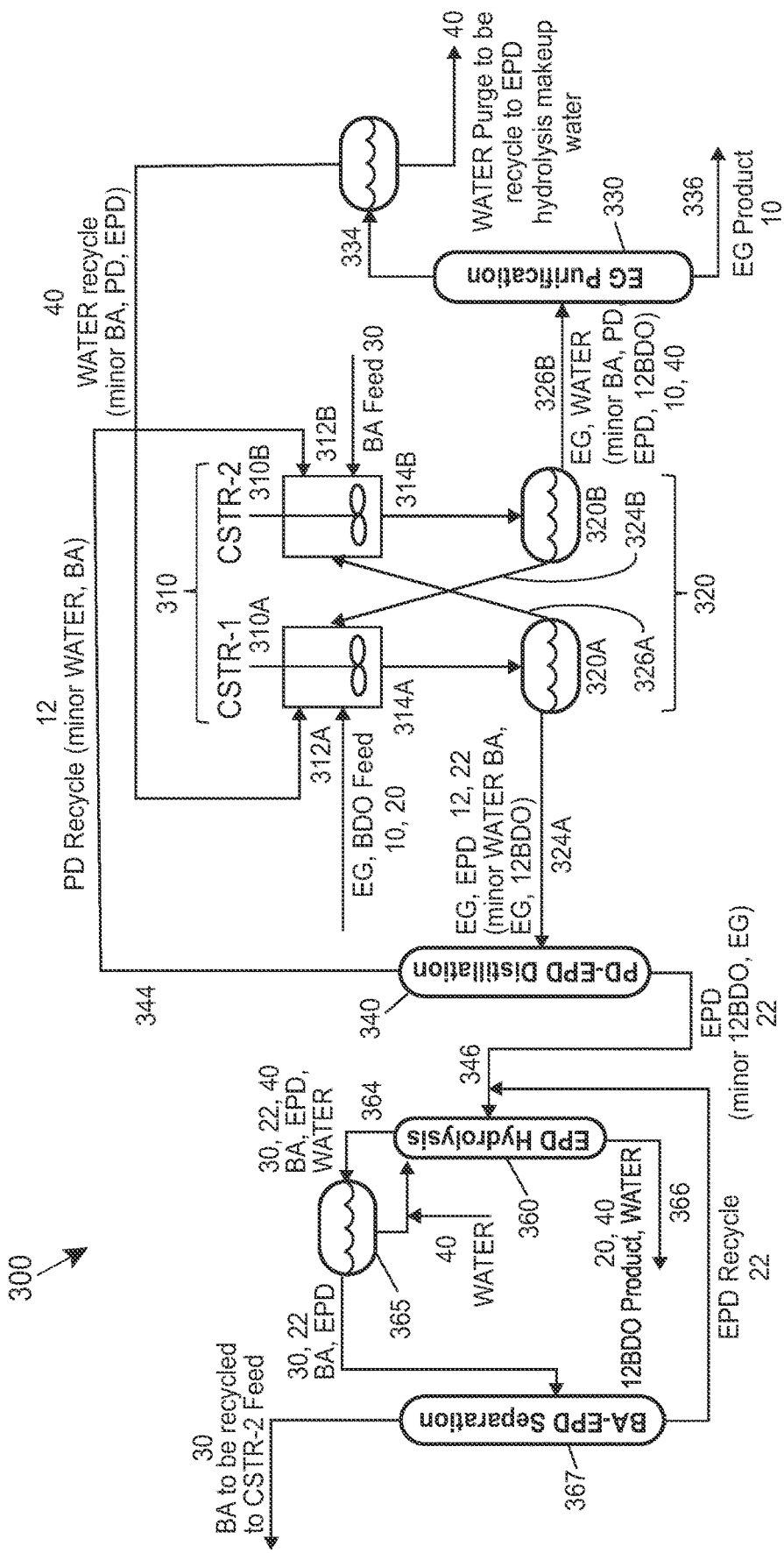
FIG. 3 is a process flow diagram illustrating a method for separating polyols according to a third aspect of the disclosure.
Figure 4:
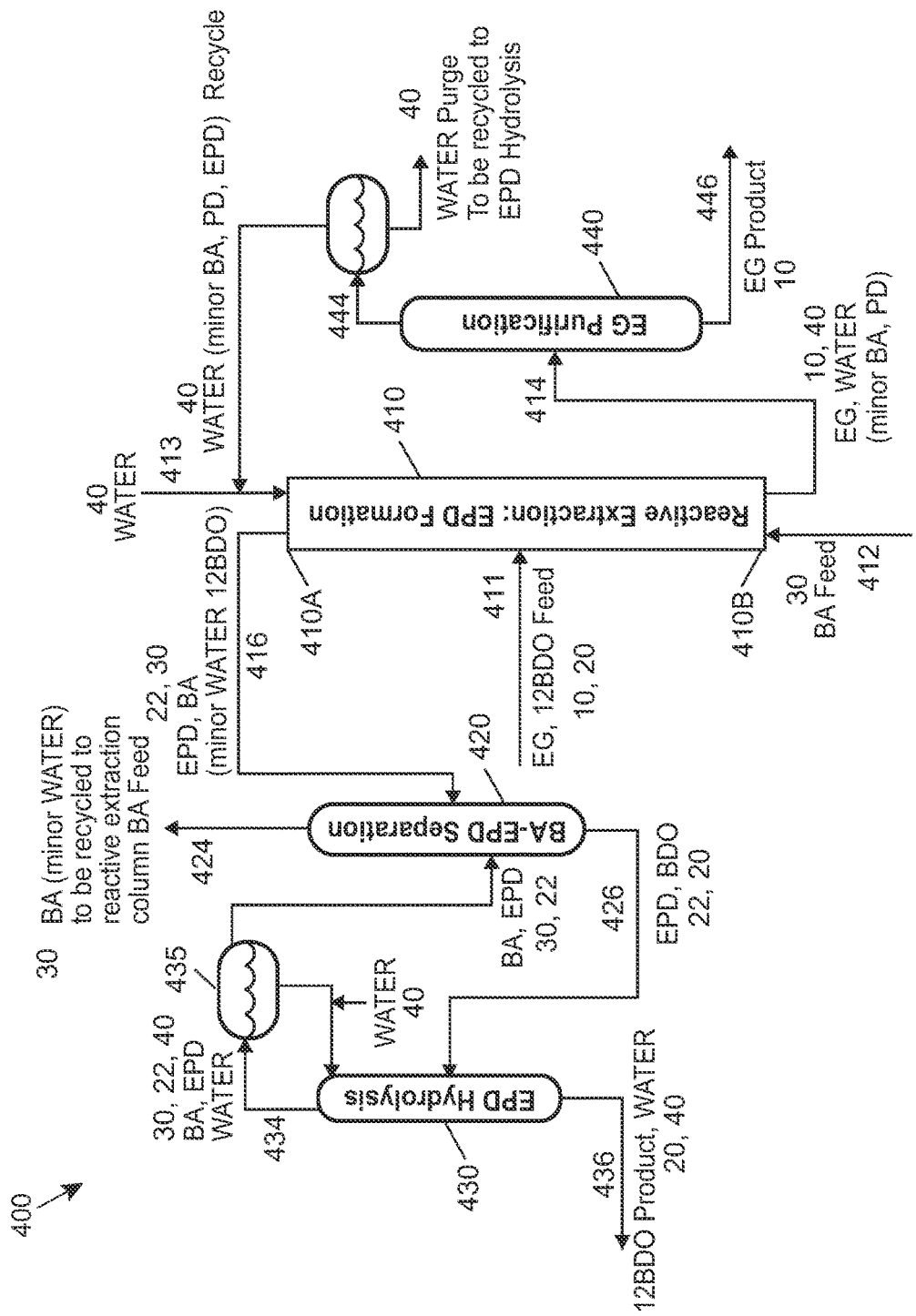
FIG. 4 is a process flow diagram illustrating a method for separating polyols according to a fourth aspect of the disclosure.

FIGS. 1-4 illustrate methods 100, 200, 300, 400 for separating polyol mixtures according to several aspects of the disclosure. A first polyol reactant 10, a second polyol reactant 20, and an acetalization reactant 30 are generally fed to a reactor 110, 210, 310, 410, whereupon an acid-catalyzed reaction is performed to form at least one of a first acetalization product 12 as a reaction product between the first polyol reactant 10 and the acetalization reactant 30, and a second acetalization product 22 as a reaction product between the second polyol reactant 20 and the acetalization reactant 30. The first and second acetalization products 12, 22 generally have favorable boiling point differences or solubility differences with respect to each other and/or the first and second polyol reactants 10, 20, which facilitates separation as compared to the original first and second polyol 10, 20 mixture. Once separated, the first and/or second acetalization products 12, 22 are hydrolyzed back to their corresponding first and second polyol reactants 10, 20. FIG. 1 illustrates a first method 100 according to an aspect of the disclosure in which a two-phase continuous stirred reactor (CSTR) 110 or two batch reactors are used for acetalization. The reaction of the acetalization reactant 30 allows for a liquid-liquid phase equilibrium where the two products 12, 22 can be separated by decanting. Then each acetalization product 12, 22 can be hydrolyzed back to polyols 10, 20 via reactive distillation. FIG. 2 illustrates a second method 200 according to an aspect of the disclosure in which a reactive distillation column 210 is used for the removal of only the more volatile of the two acetalization products 12, 22. The heavier acetalization product is essentially "trapped" within the column and forced downward, where it can be hydrolyzed in the lower stages of the column. FIG. 3 illustrates a third method 300 according to an aspect of the disclosure in which acetalization is performed in one or two counter-current flow CSTRs 310 where the diol mixture 10, 20 and water 40 enter the first reactor 310A and the acetalization reactant 30 and acetalization product 12 of a particular diol 10 enter the second reactor 310B. Using reaction equilibrium principles by loading the reactor 310 with one of the acetalization products 12, the reaction system drives the complete conversion of the other diol into the desired acetalization product 22. FIG. 4 illustrates a fourth method 400 according to an aspect of the disclosure in which mixed diols 10, 20 are fed to an extraction column 410 in the center of the column, and acetalization reactant 30 is fed at the bottom of the column, and water 40 is fed to at the top of the column. Selective formation of the more favorable acetalization product 12 or 22 takes place due to the limited amount of acetalization reactant 30 present. Only the more favorable diol 10 or 20 will be able to convert to its acetalization product 12 or 22. Separation occurs through extraction based on solubility, with the diol 10 or 20 that prefers the aqueous phase separating from the acetalization product 12 or 22 that prefers the organic phase.

The process flow diagrams of FIGS. 1-4 are illustrated for the particular case of separating ethylene glycol (EG) as the first polyol reactant 10 and 1,2-butanediol (BDO or 12BDO) as the second polyol reactant 20, but they more generally apply to the disclosed methods for polyol separation. In particular, various process streams in the process flow diagrams can be generalized such that ethylene glycol (EG), 1,2-butanediol (BDO or 12BDO), butyraldehyde (BA), 2-propyl-1,3-dioxolane (PD; EG+BA), and 4-ethyl-2-propyl-1,3-dioxolane (EPD; 12BDO+BA) more generally correspond to the first polyol reactant 10, the second polyol reactant 20, the acetalization reactant 30, the first acetalization product 12, and the second acetalization product 22, respectively. Streams can generally consist of or consist essentially of their indicated components (e.g., up to 0.1, 1, 2, or 5 wt. % of components other than the indicated components). Components indicated as minor components can be absent from the stream or present in minor or residual amounts (e.g., up to 0.01, 0.1, 1, 2, or 5 wt. % of each minor component).

The "first" and "second" labels as used herein for the polyol reactants 10, 20 and the acetalization products 12, 22 are arbitrary with respect to the particular chemical species represented in a process. Suitably, however, the "first" and "second" polyol reactants 10, 20 and acetalization products 12, 22 can be designated based on the first acetalization product 12 having a lower boiling point than that the second acetalization product 22, for example such that the first acetalization product 12 can be recovered in a distillate stream of a distillation column and the second acetalization product 22 can be recovered in a bottoms stream of the distillation column.

FIG. 1 illustrates a first method 100 for separating polyols according to a first aspect of the disclosure. The method includes feeding 112 to a reactor 110 (i) a first polyol 10 reactant having 2 to 10 carbon atoms and having at least two hydroxyl groups on adjacent carbon atoms (i.e., a first vicinal diol), (ii) a second polyol reactant 20 different from the first polyol reactant 10, having 2 to 10 carbon atoms, and having at least two hydroxyl groups on adjacent carbon atoms (i.e., a second, different vicinal diol), (iii) an acetalization reactant 30, and (iv) (optionally) water 40. The reactor 110 can generally be a continuous, batch, or semi-batch reactor (e.g., such as a continuous stirred tank reactor (CSTR) or other reactor 110 as shown in the FIG. 1), and suitably the reactor 110 is not a reactive distillation column. The acetalization reactant 30 includes one or more of an aldehyde having 1 to 10 or 3 to 10 carbon atoms and a ketone having 3 to 10 or 4 to 10 carbon atoms. In some embodiments, water 40 is avoided in the reactor feed 112, for example containing not more than 5 wt. % water (e.g., up to 0.1, 1, 2, or 5 wt. % water in the fresh feed streams to the reactor), which can account primarily for water generated during acetalization and recycled to the reactor 110. In some embodiments, water 40 can be added to the feed 112 streams (e.g., in addition to recycling water which is generated during acetalization), for example to serve as an extraction fluid for unreacted polyol 10, 20, which in turn allows convenient recycling of polyol 10, 20 reactant to the reactor 110. For example, in the process scheme shown in FIG. 1, addition of water 40 as an extracting agent in a decanter 120 is a possibility, as it could extract more unreacted polyol 10, 20 out for recycling, in which case the additional water 40 suitably would be removed in a following evaporator 130 before the unreacted polyols 10, 20 are returned to the reactor 40.

The method 100 in the first aspect further includes forming in the reactor 110 via an acid-catalyzed reaction: (i) a first acetalization product 12 as a reaction product between the first polyol reactant 10 and the acetalization reactant 30, (ii) a second acetalization product 22 including a reaction product between the second polyol reactant 20 and the acetalization reactant 30, and (iii) water 40. Suitably, there is at least 70, 80, 90, or 95% and/or up to 90, 95, 98, 99, or 99.5% conversion of first polyol reactant 10, for example based on a stoichiometric excess of acetalization reactant 30 relative to both/all polyol reactants 10, 20 and a corresponding unreacted excess of acetalization reactant 30 in the reactor product stream 114. Suitably, there is at least 70, 80, 90, or 95% and/or up to 90, 95, 98, 99, or 99.5% conversion of second polyol reactant 20, for example based on a stoichiometric excess of acetalization reactant 30 relative to both polyol reactants 10, 20 and a corresponding unreacted excess of acetalization reactant 30 in the reactor product stream 114. The water 40 is generally formed as an acetalization byproduct with both acetalization products 12, 22. Additional water 40 can be present from the feed 112, but which was not formed during reaction.

The method 100 in the first aspect further includes separating 120 a reactor product mixture, for example the outlet stream 114, including the first acetalization product 12, the second acetalization product 22, and the water 40 into (i) a water-immiscible product 124 including the first acetalization product 12 and the second acetalization product 22 (e.g., optionally also excess acetalization reactant 30), and (ii) an aqueous product 126 including the water 40 (e.g., optionally also unreacted first and/or second polyol reactants 10, 20). The separation can be performed by any suitable method, for example gravity-based settling (such as decanting) based on two immiscible product streams. FIG. 1 illustrates the separator 120 as a decanter with the light-phase outlet 124 as the water-immiscible product and the dense-phase outlet 126 as the aqueous product.

The method 100 in the first aspect further includes separating 140 the water-immiscible product 124 into (i) a first product 144 including the first acetalization product 12, and (ii) a second product 146 including the second acetalization product 22. This separation is suitably performed by distillation, such as in a distillation column 140 as illustrated in FIG. 1, but generally not a reactive distillation column such as with acid or other catalyst therein or fed thereto. The first acetalization product 12 can be recovered in an overhead distillate 144 stream as illustrated in FIG. 1, but could be bottoms 146 if the first acetalization product 12 is the heavier boiling acetal. The first acetalization product 12 can include the excess acetalization reactant 30. The first acetalization product 12 suitably is substantially free of second acetalization product 22, such as less than 10, 5, 2, 1, or 0.1 wt. % second acetalization product 22 relative to the first product 144 as a whole and/or relative to the combined amount of first and second acetalization products 12, 22 therein. The second acetalization product 22 can be recovered in a bottoms 146 stream as illustrated in FIG. 1, but could be distillate 144 if the second acetalization product 22 is the lighter boiling acetal. The second acetalization product 22 can include the unreacted first and/or second polyol reactants 10, 20. The second acetalization product 22 suitably is substantially free of first acetalization product 12, such as less than 10, 5, 2, 1, or 0.1 wt. % first acetalization product 12 relative to the second product 146 as a whole and/or relative to the combined amount of first and second acetalization product therein 12, 22.

The method 100 in the first aspect further includes hydrolyzing 150 the first product 144 to form the first polyol reactant 10 from the first acetalization product 12. This is illustrated in FIG. 1 in a reactive distillation column 150 with acid catalyst therein/added thereto and with hydrolysis water 40 fed thereto. An outlet 154 includes the acetalization reactant 30 and water 40, which can be separated 155 (e.g., in a decanter) to recover the acetalization reactant 30 for recycle to the reactor 110 and water 40 for recycle to the column 150. An outlet 156 includes the first polyol 10 and water 40, which can be separated 157 (e.g., in a distillation column) to recover the first polyol 10 as a final product (e.g., in substantially pure form) and water 40 for recycle to the column 150. The method 100 in the first aspect further includes hydrolyzing 160 the second product 146 to form the second polyol reactant 20 from the second acetalization product 22. This is illustrated in FIG. 1 in a reactive distillation column 160 with acid catalyst therein/added thereto and with hydrolysis water 40 fed thereto. An outlet 164 includes the acetalization reactant 30, water 40, and possibly un-hydrolyzed second acetalization product 22, which can be separated 165 (e.g., in a decanter) to recover the acetalization reactant 30 and any second acetalization product 22 for further separation 167, and water 40 for recycle to the column 160. The separator 167 (e.g., distillation column) can recover the acetalization reactant 30 for recycle to the reactor 110 (e.g., distillate) and second acetalization product 22 for recycle to the column 160. An outlet 166 includes the second polyol 20 and water 40, which can be separated (e.g., in a distillation column; not shown) to recover the second polyol 20 as a final product (e.g., in substantially pure form) and water 40 for recycle to the column 160.

The method 100 in the first aspect can further include recycling at least a portion of the aqueous product 126, for example from the separation tank 120 after the reactor 110 as illustrated in FIG. 1, as a water 40 feed to one or more unit operations. For example, water 40 can be recycled to the reactor 110 in a stream that optionally also includes unreacted first and/or second polyol reactants 10, 20. Water 40 can be recycled to a first hydrolysis apparatus 150 for hydrolyzing the first product 144, such as the reactive distillation column 150 illustrated in FIG. 1. Water 40 can be recycled to a second hydrolysis apparatus 160 for hydrolyzing the second product 146, such as the reactive distillation column 160 illustrated in FIG. 1. Suitably, the aqueous product 126 is subjected to a separation 130 step such as distillation so that water 40 substantially free from unreacted first and/or second polyol reactants 10, 20 can be used as the hydrolysis feed water, while the water 40 including unreacted first and/or second polyol reactants 10, 20 can be part of the reactor recycle for feedstock recovery by combination with the feed 112.

FIG. 2 illustrates a method 200 for separating polyols according to a second aspect of the disclosure. The method includes feeding 212 to a reactor 210 including a reactive distillation column: (i) a first polyol reactant 10 having 2 to 10 carbon atoms and having at least two hydroxyl groups on adjacent carbon atoms (i.e., a first vicinal diol), (ii) a second polyol reactant 20 different from the first polyol reactant 10, having 2 to 10 carbon atoms, and having at least two hydroxyl groups on adjacent carbon atoms (i.e., a second, different vicinal diol), (iii) an acetalization reactant 30, and (iv) water 40. The reactor 210 can be a continuous, batch, or semibatch reactive distillation column, such as illustrated in the FIG. 2. The acetalization reactant 30 includes one or more of an aldehyde having 1 to 10 or 3 to 10 carbon atoms and a ketone having 3 to 10 or 4 to 10 carbon atoms. The water 40 feed can be a component of the polyol reactant 10, 20 feed and/or as a separate feed, such as in combination with the acetalization reactant 30. The water 40 feed is provided as an excess to drive hydrolysis, in particular because the water 40 formed during acetalization alone is not generally sufficient for hydrolysis. In the illustrated embodiment, BDO acetal (e.g., EPD) formation is so thermodynamically favorable that a significant excess of water 40 is required to push the acetal formed in the reactive distillation column 210 back to BDO.

The method 200 in the second aspect further includes forming in the reactor 210 via an acid-catalyzed reaction (e.g., in a middle portion of the column): (i) a first acetalization product 12 as a reaction product between the first polyol reactant 10 and the acetalization reactant 30, (ii) a second acetalization product 22 as a reaction product between the second polyol reactant 20 and the acetalization reactant 30, and (iii) water 40, which can be formed as an acetalization byproduct with one or both acetalization products 12, 22. Suitably, there is at least 70, 80, 90, or 95% and/or up to 90, 95, 98, 99, or 99.5% conversion of first polyol reactant 10, for example based on an at least stoichiometric amount of the acetalization reactant 30 relative to the first polyol reactant 10. An object in the second aspect is to selectively acetalize the first polyol reactant 10 and not the second polyol reactant 20, so the acetalization reactant 30 is preferably in minimal stoichiometric excess relative to the first polyol reactant 10. Even when acetalization of the second polyol reactant 20 is favored (e.g., as for EG/BDO mixtures), the second polyol reactant 20 is formed by hydrolysis and recovered in reactive distillation column 210, for example in the bottoms 216 in FIG. 2, so any acetalization reactant 30 which preferentially acetalizes the second polyol reactant 20 in the reactive distillation column 210 is also recovered/re-formed in situ in the reactive distillation column 210 for reaction with the first polyol reactant 10. In general, the larger the polyol and the larger the acetalization reactant (i.e., in terms of molecular weight of each), and therefore the higher boiling point of each, the more favorable are the thermodynamics of formation of the acetal for the larger polyol (e.g., as for EG/BDO mixtures).

The reactor 210 can include one or both of a heterogeneous acid catalyst and a homogeneous acid catalyst fed to the reactive distillation column. The heterogeneous acid catalyst can be a solid acid catalyst in a portion of the reactor 210, for example by partitioning the reactor into spatial zones with and without catalyst. The homogeneous acid catalyst can be a mineral acid such as sulfuric acid. A homogeneous mineral acid catalyst such as sulfuric acid generally has low volatility and will exit the bottom of essentially any distillation column used in the disclosed methods, in which case it will ultimately end up with the purified polyol and can be recovered by precipitation with a base (e.g., sodium hydroxide or otherwise).

The method 200 in the second aspect further includes hydrolyzing in the reactor 210 via an acid-catalyzed reaction the second acetalization product 22 to re-form the second polyol reactant 20 from the second acetalization product 22. Hydrolysis can be performed in a bottom or lower portion 210A of the column 210 containing catalyst but which is locally substantially free from the acetalization reactant 30, which is generally more volatile and moves upward towards the distillate 214.

The method 200 in the second aspect further includes removing from the reactor 210 (i) a first product 214 including the first acetalization product 12, for example as the distillate 214 in FIG. 2, and (ii) a second product 216 including the re-formed second polyol reactant 20, for example as the bottoms 216 in FIG. 2. The first product 214 can include excess acetalization reactant 30 and/or (hydrolysis) water 40. The first product 214 can be substantially free of second acetalization product 22, such as less than 10, 5, 2, 1, or 0.1 wt. % second acetalization product 22 relative to the first product 214 as a whole and/or relative to the combined amount of first and second acetalization product 12, 22 therein. The second product 216 can be substantially free of first acetalization product 12, such as less than 10, 5, 2, 1, or 0.1 wt. % first acetalization product 12 relative to the second product 216 as a whole and/or relative to the combined amount of first and second acetalization product 12, 22 or polyol reactant 10, 20 therein. The second product 216 can represent the second polyol 20 as a final product (e.g., in substantially pure form).

The method 200 in the second aspect further includes hydrolyzing 220 the first product 214 to form the first polyol reactant 10 from the first acetalization product 12. Hydrolysis can be performed in a reactive distillation column 220 as shown in FIG. 2 with acid catalyst therein/added thereto and with hydrolysis water 40 fed thereto. An outlet 224 includes the acetalization reactant 30 and water 40, which can be separated 225 (e.g., in a decanter) to recover the acetalization reactant 30 for recycle to the reactor 210 and water 40 for recycle to the column 220. An outlet 226 includes the first polyol 10 and water 40, which can be separated 227 (e.g., in a distillation column) to recover the first polyol 10 as a final product (e.g., in substantially pure form) and water 40 for recycle to the column 210 and/or column 220.

FIG. 3 illustrates a method 300 for separating polyols according to a third aspect of the disclosure. The method 300 includes feeding 312A, 312B to a reactor 310 (*i*) a first polyol reactant 10 having 2 to 10 carbon atoms and having at least two hydroxyl groups on adjacent carbon atoms (i.e., a first vicinal diol), (ii) a second polyol reactant 20 different from the first polyol reactant 10, having 2 to 10 carbon atoms, and having at least two hydroxyl groups on adjacent carbon atoms (i.e., a second, different vicinal diol), (iii) an acetalization reactant 30, (iv) a first acetalization product 12 including a reaction product between the first polyol reactant 10 and the acetalization reactant 30, and (v) (optionally) water 40. The reactor 310 can generally be a continuous, batch, or semibatch reactor (e.g., such as a continuous stirred tank reactor (CSTR-1) or other reactor 310A as shown in the FIG. 3), and suitably the reactor 310 is not a reactive distillation column. The acetalization reactant 30 includes one or more of an aldehyde having 1 to 10 or 3 to 10 carbon atoms and a ketone having 3 to 10 or 4 to 10 carbon atoms. For the illustrative EG/BDO case as the first and second polyols 10, 20, respectively, BDO is the favored polyol for acetalization, and the product addition utilizes the less kinetically favored EG acetal (PD) as the recycled first acetalization product 12. In general, it is preferred to recycle the less kinetically favored acetalization product as the first acetalization product 12, because comparatively less first acetalization product 12 recycle is used for sufficient product addition to inhibit further first polyol 10 conversion while still favoring second polyol 20 conversion. In other embodiments, however, it is possible to recycle the more kinetically favored acetalization product as the first acetalization product 12, for example with correspondingly higher recycle rates and/or switching distillate/bottoms streams in the separation column. In some embodiments, water 40 can be added to the feed streams 312A, 312B (e.g., in addition to recycling water which is generated during acetalization and/or recovered in polyol purification), for example to serve as an extraction fluid for unreacted polyol 10, 20, which in turn allows convenient recycling of polyol reactant 10, 20 to the reactor 310. Although the excess water 40 eventually will be separated in a purification column 330 recovering the first polyol 10 with increased energy costs, the excess water 40 is nonetheless a good way to improve phase separation efficiency in a decanter 320A, 320B.

The method 300 in the third aspect further includes forming in the reactor 310 via an acid-catalyzed reaction: (i) (optionally) further first acetalization product 12 including a reaction product between the first polyol reactant 10 and the acetalization reactant 30, (ii) a second acetalization product 22 including a reaction product between the second polyol reactant 20 and the acetalization reactant 30, and (iii) water 40. In some embodiments, there is at least 0.01, 0.1, or 1% and/or up to 1, 2, 5, or 10% conversion of first polyol reactant 10, but preferably as low as possible based on product addition inhibition of the first acetalization product 12 fed to the reactor and the equilibrium nature of the reaction. Suitably, there is at least 70, 80, 90, or 95% and/or up to 90, 95, 98, 99, or 99.5% conversion of second polyol reactant 20, for example based on an at least stoichiometric amount of acetalization reactant 30 relative to the second polyol reactant 20. The water 40 is generally formed as an acetalization byproduct with one or both acetalization products 12, 22. Additional water 40 can be present from the feed, but which was not formed during reaction.

The method 300 in the third aspect further includes separating 320, 320A a reactor product mixture 314A including the first acetalization product 12, the second acetalization product 22, the first polyol reactant 10 (e.g., at least 90, 95, 98, or 99% of that fed to the reactor), and the water 40 into (i) a water-immiscible product 324A including the first acetalization product 12, the second acetalization product 22, and optionally also excess acetalization reactant 30, and (ii) an aqueous product 326A including the first polyol reactant 10, the water 40, and optionally also unreacted second polyol reactant 20. The separation can be gravity-based settling such as decanting, based on two immiscible product streams as illustrated in FIG. 3 by a first decanter vessel 320A below the first reactor 310A (CSTR-1).

The method 300 in the third aspect further includes separating 340 the water-immiscible product 324A into (i) a first product 344 including the first acetalization product 12 (e.g., in the distillate), and (ii) a second product 346 including the second acetalization product 22 (e.g., in the bottoms). Separation can be performed by distillation, such as in a distillation column 340 as illustrated in FIG. 3, but generally not a reactive distillation column such as with acid or other catalyst therein or fed thereto. The first product 344 can include the excess acetalization reactant 30. The first product 344 can be substantially free of second acetalization product 22, such as less than 10, 5, 2, 1, or 0.1 wt. % second acetalization product 22 relative to the first product 344 as a whole and/or relative to the combined amount of first and second acetalization product 12, 22 therein. The second product 346 can include the unreacted first and/or second polyol reactants 10, 20. The second product 346 can be substantially free of first acetalization product 12, such as less than 10, 5, 2, 1, or 0.1 wt. % first acetalization product 12 relative to the second product 346 as a whole and/or relative to the combined amount of first and second acetalization product 12, 22 therein.

The method 300 in the third aspect further includes hydrolyzing 360 the second product 346 to form the second polyol reactant 20 from the second acetalization product 22. Hydrolysis can be performed in a reactive distillation column 360 as shown in FIG. 3 with acid catalyst therein/added thereto and with hydrolysis water 40 fed thereto. An outlet 364 includes the acetalization reactant 30, water 40, and possibly un-hydrolyzed second acetalization product 22, which can be separated 365 (e.g., in a decanter) to recover the acetalization reactant 30 and any second acetalization product 22 for further separation 367, and water 40 for recycle to the column 360. The separator 367 (e.g., distillation column) can recover the acetalization reactant 30 for recycle to the reactor 310 (e.g., distillate to the second reactor 310B) and second acetalization product 22 for recycle to the column 360. An outlet 366 includes the second polyol 20 and water 40, which can be separated (e.g., in a distillation column; not shown) to recover the second polyol 20 as a final product (e.g., in substantially pure form) and water 40 for recycle to the column 360.

The method 300 in the third aspect can further include recycling the first product 344 including the first acetalization product 12 to the reactor 310. In FIG. 3, this can correspond to PD-EPD distillation overhead product or distillate 344 being recycled directly back to the reactor 310, for example to the second reactor 310B (CSTR-2) as shown, or directly to the first reactor 310A (CSTR-1) and without necessarily including the second reactor 310B (CSTR-2) (not shown).

In a particular embodiment illustrated by FIG. 3, the method 300 in the third aspect can further include feeding 312B to a second reactor 310B: (i) the first product 344 including the first acetalization product 12 such as from the PD-EPD column 340, (ii) the acetalization reactant 30, and (iii) the aqueous product 326A including the first polyol reactant 10 and the water 40 such as from the decanter tank 320A at the outlet 314A of the first reactor 310A (CSTR-1) in FIG. 3. The second reactor 310B can be a continuous, batch, or semibatch reactor, such as CSTR-2 in FIG. 3, and the second reactor 310B suitably is not a reactive distillation column. In this case, the method 300 can further include forming in the second reactor 310B via an acid-catalyzed reaction: (i) (optionally) the first acetalization product 12 including a reaction product between the first polyol reactant 10 and the acetalization reactant 30, and (ii) the second acetalization product 22 including a reaction product between the second polyol reactant 20 (e.g., as recycled from the first reactor 310A) and the acetalization reactant 30 (e.g., as freshly fed to the second reactor 310B). Suitably, there is at least 70, 80, 90, or 95% and/or up to 90, 95, 98, 99, or 99.5% conversion of second polyol reactant 20. An object of the second reactor 310B is to react any remaining second polyol 20 from the first reactor 310A, while at the same time acetalizing little or no first polyol 10, but instead hydrolyzing some of the recycled first acetalization product 12, so that the concentration of the first polyol 10 in the aqueous stream 326B from a second separator 320B, such as a decanter as shown in FIG. 3 below the second reactor 310B (CSTR-2), is as high as possible. Thus, the method 300 can further include separating 320B a second reactor product mixture 314B including the first polyol 10, the second acetalization product 22, the acetalization reactant 30, and the water 40 into (i) a second water-immiscible product 324B including the second acetalization product 22 and the acetalization reactant 30, and (ii) a second aqueous product 326B including the first polyol 10 and the water 40. Separation can be gravity-based settling such as decanting, based on two immiscible product streams, as illustrated by the second decanter 320B. The second water-immiscible product 324B can then be fed to the first reactor 310A (CSTR-1). The second aqueous product 326B can be separated 330 (e.g., in a distillation column) to recover the first polyol 10 as a final product (e.g., in substantially pure form) in a bottoms stream 336 and water 40 in an overhead stream 334 for recycle to the reactor 310 or hydrolysis reactor 340.

FIG. 4 illustrates a method 400 for separating polyols according to a fourth aspect of the disclosure. The method 400 includes feeding 411, 412, 413 to a reactor 410 including a reactive extraction vessel (i) a first polyol reactant 10 having 2 to 10 carbon atoms and having at least two hydroxyl groups on adjacent carbon atoms (i.e., a first vicinal diol), (ii) a second polyol reactant 20 different from the first polyol reactant 10, having 2 to 10 carbon atoms, and having at least two hydroxyl groups on adjacent carbon atoms (i.e., a second, different vicinal diol), (iii) an acetalization reactant 30, which can also serves as an extraction fluid in this aspect, and (iv) water 40.

The reactive extraction vessel 410 can generally be a continuous, batch, or semibatch reactive extraction vessel or column as illustrated in FIG. 4. The acetalization reactant 30 includes one or more of an aldehyde having 1 to 10 or 3 to 10 carbon atoms and a ketone having 3 to 10 or 4 to 10 carbon atoms. The water 40, which is in addition to any water formed during reaction, can serve as an extraction fluid in countercurrent flow with respect to the acetalization reactant 30 extraction fluid, such as with the water 40 fed 413 at the top 410A and the acetalization reactant 30 fed 412 at the bottom 410B as illustrated for the reactive extraction column in FIG. 4. The first and second polyol reactants 10, 20 can be fed 411 at any suitable location in the column 410.

The method 400 in the fourth aspect further includes forming in the reactor 410 via an acid-catalyzed reaction (i) (optionally) a first acetalization product 12 including a reaction product between the first polyol reactant 10 and the acetalization reactant 30, (ii) a second acetalization product 22 including a reaction product between the second polyol 20 reactant and the acetalization reactant 30, and (iii) water 40. There can be at least 0.01, 0.1, or 1% and/or up to 1, 2, 5, or 10% conversion of first polyol reactant 10, but suitably the first polyol 10 conversion is as low as possible based on the first acetalization product 12 being the less favored acetalization product and the limiting amount of acetalization reactant 30 fed to the reactor. Suitably, there is at least 70, 80, 90, or 95% and/or up to 90, 95, 98, 99, or 99.5% conversion of second polyol reactant 20, for example based on a stoichiometric amount or slight excess of acetalization reactant 30 relative to the second polyol reactant 20. The water 40 present in the reactor 410 can include both (a) water 40 formed as an acetalization byproduct with one or both acetalization products 12, 22 and (b) water 40 fed 413 as part of the extraction fluid feed to the reactor 410, but which was not formed during reaction.

The reactor/reactive extraction vessel 410 can include one or both of a heterogeneous acid catalyst and a homogeneous acid catalyst fed to the reactive distillation column 410. The heterogeneous acid catalyst can be a solid acid catalyst in a portion of the reactor 410, for example by partitioning the reactor into spatial zones with and without catalyst. The homogeneous acid catalyst can be a mineral acid such as sulfuric acid. A homogeneous mineral acid catalyst such as sulfuric acid generally has low volatility and will exit the bottom of essentially any distillation column used in the disclosed methods, in which case it will ultimately end up with the purified polyol and can be recovered by precipitation with a base (e.g., calcium hydroxide, sodium hydroxide or otherwise).

The method 400 in the fourth aspect further includes removing from the reactor (i) a first product 414 including the first polyol reactant 10 and the water 40 (e.g., aqueous extract), and (ii) a second product 416 including the second acetalization product 22 and the acetalization reactant 30 (e.g., organic extract). The first product 414 or aqueous extract suitably is substantially free of second acetalization product 22, such as less than 10, 5, 2, 1, or 0.1 wt. % second acetalization product 22 relative to the first product 414 as a whole and/or relative to the combined amount of first polyol reactant 10 and second acetalization product 22 therein. The first product 414 can be separated 440 (e.g., in a distillation column) to recover the first polyol 10 in a bottoms stream 446 as a final product (e.g., in substantially pure form) and water 40 in an overhead stream 444 for recycle to the reactor 410 or hydrolysis reactor 430. The second product 416 or organic extract suitably is substantially free of first acetalization product 12 and/or first polyol reactant 10, such as less than 10, 5, 2, 1, or 0.1 wt. % first acetalization product 12 and/or first polyol 10 reactant relative to the second product 416 as a whole and/or relative to the combined amount of second acetalization product 22 or polyol reactant 10, 20 therein.

The method 400 in the fourth aspect generally uses at least a stoichiometric limiting amount of acetalization reactant 30 to selectively convert only the second polyol reactant 20, with the acetalization reactant 30 also serving as an organic extraction fluid to recover the second product 416, for example exiting the top 410A of the extraction column 410 as illustrated in FIG. 4. In the illustrative system for EG (first polyol 10) and BDO (second polyol 10) separation using BA (acetalization reactant 30), the EPD (second acetalization product 22) is essentially insoluble in water 40 and forms quickly and nearly completely with excess BA present. Thus, essentially all the BDO fed will convert to EPD which will transfer to the organic (upflowing) phase. The EG fed will transfer to the aqueous phase (e.g., water 40 fed 413 as the aqueous extraction fluid) and also partially convert to PD (first acetalization product 12), but as the PD moves upwards it will hydrolyze back to EG (first polyol 10) which will transfer to the aqueous phase. Maintaining a low concentration of BA (acetalizing reactant 30) will help form the organic layer, but that organic layer will be composed mostly of EPD (second acetalization product 22) approaching the top 410A of the column 410. There suitably is a balance in the quantity of BA added: A sufficient amount is added to acetalize all the BDO feed and maintain the organic phase (which could be equal to or larger than the stoichiometric limiting amount), but not so much as to acetalize a significant portion of the EG.

The method 400 in the fourth aspect further includes hydrolyzing 430 the second product 416 to form the second polyol reactant 20 from the second acetalization product 22. Hydrolysis can be performed in a reactive distillation column 430 with acid catalyst therein/added thereto and with hydrolysis water 40 fed thereto, for example with prior distillation 420 or other removal of acetalization reactant 30 therein. As more particularly illustrated in FIG. 4, the second product 416 is fed to the distillation column 420 to recover the acetalization reactant 30 in an overhead stream 424 and the second acetalization product 22 along with any unreacted second polyol 20 in a bottoms stream 426. The bottoms stream 426 is fed to the reactive distillation column 430 to hydrolyze the second acetalization product 22. An overhead outlet 434 includes the acetalization reactant 30, water 40, and possibly un-hydrolyzed second acetalization product 22, which can be separated 435 (e.g., in a decanter) to recover the acetalization reactant 30 and any second acetalization product 22 for recycle to the column 420, and water 40 for recycle to the column 430. A bottoms outlet 436 includes the second polyol 20 and water 40, which can be separated (e.g., in a distillation column; not shown) to recover the second polyol 20 as a final product (e.g., in substantially pure form) and water 40 for recycle to the column 430.

EXAMPLES

The following examples illustrate the disclosed methods, but are not intended to limit the scope of any claims thereto. The examples are based on reversible acetal formation from diols with essentially no net consumption of aldehyde or water. The examples illustrate various steps and unit operations in the disclosed methods, including acetal formation, acetal hydrolysis, and acetal separation.

Acetal Formation

Selective Acetal Formation with Product Addition: A representative reaction system includes a feed stream with 20 wt. % 1,2-butanediol (BDO) and 80 wt. % 1,2-ethanediol (ethylene glycol; EG) and uses butyraldehyde (BA) as the acetalization agent. Further, the relative values of the reaction equilibrium constants and the liquid-liquid phase equilibrium for this system suggest that the selective acetalization of BDO in a series of stirred tank reactors is particularly suitable for separation of the EG/BDO feed. By using 2-propyl-1,3-dioxolane (PD), the product of the EG+BA reaction, as an organic extracting agent in a stirred reactor, the reaction of EG with BA is inhibited because of thermodynamic constraints, while 4-ethyl-2-propyl-1,3-dioxolane (EPD), the product of the BDO+BA reaction, is formed and immediately extracted into PD, thus facilitating complete removal of BDO from EG. In illustrative experiments, PD was placed into a batch reactor along with the EG/BDO mixture (about 80:20 w/w EG:BDO), BA (30% molar excess relative to BDO), and/or some water. Results at equilibrium are summarized in Table 1 below. Run R9 showed 90% conversion of BDO to EPD and only 1.5% conversion of EG to PD. For run R10, the organic (top) product layer included 1% EG, 0.1% BDO, 15.7% BA, 22.7% H2O, 43.8% PD, and 16.8% EPD (all mol. %); and the polar/aqueous (bottom) product layer included 6.6% EG, 0.05% BDO, 0.6% BA, 92.4% H2O, 0.3% PD, and 0.01% EPD (all mol. %). This selective acetal formation is illustrated in the general process diagram of FIG. 3, which includes product addition of the first acetalization product 12 (PD) to the reactor 310, for example as an overhead recycle stream 344 from the distillation column 340 separating the first acetalization product 12 from the second acetalization product 22 (EPD).

TABLE 1

Initial Quantities and Polyol Conversion for Product Addition Experiments

| Exp. | Initial Species Molar Quantities | | | | | EG Conversion (%) | BDO Conversion (%) |
| --- | --- | --- | --- | --- | --- | --- | --- |
| | EG | BDO | BA | H2O | PD | | |
| R8 | 5 | 1 | 1.3 | | 2 | 2 | 80 |
| R9 | 5 | 1 | 1.3 | | 5 | 1.5 | 90 |
| R10 | 0.43 | 0.09 | 0.5 | 2.55 | | 50 | 98 |

Selective Acetal Formation with Limiting Acetalization Reactant: A reaction using an initial diol mixture of composition 77.5 wt % EG and 22.5 wt % BDO (83.3 mol % EG and 16.7 mol % BDO) was conducted at the one-mole scale wherein incremental quantities of BA were added followed by stirring for 24 hr. Paratoluenesulfonic acid at a concentration of 0.5 wt % of total solution was used as the catalyst. An initial quantity of BA at a molar ratio of BA:(EG+BDO) of 0.22:1 was used. The mixture was allowed to come to equilibrium and the composition of each phase present was analyzed by GC. Additional increments of BA (0.11 mol/mol (EG+BDO)) were then added and the composition of each phase was analyzed after the reaction was allowed to come to equilibrium. Table 2 summarizes the reactant quantities and product phases/conversions for the experiments. Table 3 summarizes the component concentrations of the product top (organic) phase and product bottom (aqueous) phase. The results show that unreacted diols stay in a diol/water rich phase, and the acetals formed are almost entirely present in an organic (acetal-rich) phase as the upper layer of the product mixture. Incremental addition of BA increases the conversion of BDO faster than that of EG, such that at the maximum amount of BA added (R5-7) the BDO conversion is 99% while the EG concentration is only 56%. This illustrates that it is possible to selectively react BDO away from EG by adding an appropriate quantity of BA. Furthermore, the unreacted EG remains as a separate phase from the acetal where it can be simply decanted away. In this way, nearly one-half of the EG in the feed mixture can be recovered without derivatization. This selective acetal formation is illustrated in the general process diagram of FIG.

4, which includes reactive extraction in the column 410 to with a stoichiometric limiting amount of acetalization reactant 30 (BA) relative to the second polyol 20 (BDO), resulting in selective conversion of the second polyol 20 to the second acetalization product 22 (EPD) and extraction/recovery of the unreacted first polyol 10 (EG) in an aqueous stream.

TABLE 2

Feed materials, conditions, and diol conversions for mixed EG/BDO feed with incremental BA addition (phases: top is acetal-rich; bottom is EG/H2O-rich)

| Run # | Temp (° C.) | Number of Moles in Initial Reaction Mixture | | | Estimated Quantity of Phases Present (g) | Diol Conversion | |
|---|---|---|---|---|---|---|---|
| | | EG | BDO | BA | | EG | BDO |
| R5-1 | 25 | 1.539 | 0.308 | 0.415 | Top 38.2 Bottom 114.9 | 0.10 | 0.62 |
| R5-3 | 25 | 1.539 | 0.308 | 0.613 | Top 65.8 Bottom 105.9 | 0.19 | 0.78 |
| R5-5 | 25 | 1.539 | 0.308 | 0.813 | Top 88.3 Bottom 90.5 | 0.32 | 0.91 |
| R5-6 | 25 | 1.539 | 0.308 | 1.012 | Top 112.5 Bottom 79.3 | 0.44 | 0.97 |
| R5-7 | 25 | 1.555 | 0.311 | 1.218 | Top 127.4 Bottom 65.6 | 0.56 | 0.987 |

TABLE 3

Species concentrations in product phases of mixed EG/BDO feed with incremental BA addition (phases: T = top (acetal-rich) layer; B = bottom (EG/H2O-rich) layer)

| Sample | layer T (° C.) | Species Concentrations (mmol/g) | | | | | | | | Total (mmol/g) |
|---|---|---|---|---|---|---|---|---|---|---|
| | | BA | Water | PD | EPD1 | EPD2 | Unknown | EG | BDO | |
| R5-T1 | 25 | 0.011 | 0.042 | 3.189 | 3.096 | 1.539 | 0.000 | 0.163 | 0.026 | 8.07 |
| R5-B1 | 25 | 0.012 | 3.365 | 0.282 | 0.081 | 0.043 | 0.000 | 11.999 | 1.004 | 16.79 |
| R5T3 | 25 | 0.030 | 0.147 | 4.015 | 2.382 | 1.102 | 0.000 | 0.153 | 0.017 | 7.85 |
| R5B3 | 25 | 0.029 | 5.318 | 0.341 | 0.063 | 0.030 | 0.000 | 11.606 | 0.638 | 18.02 |
| R5T5 | 25 | 0.070 | 0.525 | 5.178 | 1.991 | 1.135 | 0.000 | 0.430 | 0.016 | 9.34 |
| R5B5 | 25 | 0.052 | 8.447 | 0.324 | 0.032 | 0.018 | 0.000 | 11.207 | 0.285 | 20.37 |
| R5T6 | 25 | 0.133 | 0.580 | 5.817 | 1.699 | 0.930 | 0.002 | 0.157 | 0.000 | 9.32 |
| R5B6 | 25 | 0.074 | 11.778 | 0.302 | 0.018 | 0.011 | 0.000 | 10.626 | 0.123 | 22.93 |
| R5T7 | 25 | 0.245 | 0.866 | 6.659 | 1.551 | 0.835 | 0.005 | 0.143 | 0.000 | 10.30 |
| R5B7 | 25 | 0.100 | 17.277 | 0.307 | 0.020 | 0.013 | 0.000 | 10.131 | 0.063 | 27.91 |

Note:
Total EPD concentration is the sum of its two stereoisomers (EPD1 and EPD2 above).

Complete Acetal Formation: An ASPENPLUS simulation of the process illustrated in FIG. 1 was performed. The representative process simulated complete conversion of the EG and BDO diols to their corresponding PD and EPD acetals with BA as the acetalization reactant in the reactor 110. Subsequent distillation 120 to separate PD and EPD followed by PD hydrolysis 150 and purification 157 as well as EPD hydrolysis 160 and purification 167 yielded a simulated EG product purity of 99.95 wt. % and a simulated BDO product purity of about 90 wt. %.

Acetal Hydrolysis

Continuous Acetal Hydrolysis: Continuous hydrolysis of EPD to BDO was successfully carried out in a 2.5 cm×1.5 m packed distillation column (stainless steel dumped packing, 0.41 cm size). For this EPD hydrolysis experiment, a 1.0 wt % H2SO4 solution in water and a stream of pure EPD were fed at the top of the distillation column in a H2O:EPD molar feed ratio of 8.5:1. A reflux ratio of L/D=15 was used in the column operation. The overall material balances for the continuous EPD hydrolysis experiment, averaged over the steady state period of the experiment, are given in Table 4 below. Recovery of the BDO was 91.5%, recovery of the BA was 98%, and recovery of water was 103%. The conversion of EPD to BDO in the continuous hydrolysis experiment was 84%. This system was modeled in ASPEN-PLUS process simulation software with similar results. The successful hydrolysis of EPD assures that similar hydrolysis of PD to reform EG is also feasible, as the equilibrium constant for PD hydrolysis is much larger than the equilibrium constant for EPD hydrolysis to BDO. More generally, the results show that hydrolysis of the first and second acetalization products 12, 22 can be performed according to various embodiments of the disclosure, for example as illustrated in FIG. 1 (columns 150 and 160), FIG. 2 (column 220), FIG. 3 (column 360), and FIG. 4 (column 430).

TABLE 4

Steady state total mass and molar species balances for EPD hydrolysis

| Stream | Total mass flow (g/min) | Species Molar Flows (mmol/min) | | | |
|---|---|---|---|---|---|
| | | EPD | H2O | BA | BDO |
| Feed 1: 1.0 wt % | 2.36 | | 130 | | |

TABLE 4-continued

Steady state total mass and molar species balances for EPD hydrolysis

| Stream | Total mass flow (g/min) | Species Molar Flows (mmol/min) | | | |
|---|---|---|---|---|---|
| | | EPD | H2O | BA | BDO |
| H2SO4 in H2O | | | | | |
| Feed 2: EPD | 2.25 | 15.3 | | | |
| Distillate | 1.02 | | | 7.2 | 12.6 |
| Bottoms | 3.58 | | 2.4 | 115 | 11.6 |

Batch Acetal Hydrolysis: Two experiments were performed to demonstrate the hydrolysis of PD and EPD and selective recovery of BA. Reactions were carried out in a 250 ml round-bottom flask with a 40 cm Vigreux column, a reflux condenser, and a still head attached for sample and product collection. The experiments were conducted with the reflux condenser temperature at 70° C. for PD hydrolysis and 69° C. for EPD hydrolysis. The initial quantities of reactants added to the flask (approximately a 10:1 molar ratio of H2O:acetal) and the quantities of product obtained are given in Table 5 below. The PD used was approximately 95% pure; EPD was >98% purity. An AMBERLYST 15 ("A15") strong cation exchange resin in the H-form was used as the catalyst for the hydrolysis reaction. Compositions of the distillate and pot residue are given in Table 6 along with a summary of the percentage of initial butyraldehyde, diol, and water in the products. The results show that hydrolysis of the first and second acetalization products 12, 22 can be readily carried out with a reasonable excess of water (approximately 10:1 initial molar ratio H2O:acetal) according to various embodiments of the disclosure, for example as illustrated in FIG. 1 (columns 150 and 160), FIG. 2 (column 220), FIG. 3 (column 360), and FIG. 4 (column 430).

TABLE 5

Initial quantities of reactants and quantities of products formed in batch hydrolysis

| Experiment | Initial quantity reactants (g) | | Quantity of products (g) | |
|---|---|---|---|---|
| PD Hydrolysis (R11) | H2O | 89 g | Distillate | 39.3 g |
| | PD | 59 g | Pot residue | 106.5 g (w/A15) |
| | A15 | 3.0 g | TOTAL | 145.8 g |
| | TOTAL | 151 g | | |
| EPD Hydrolysis (R12) | H2O | 90 g | Distillate | 36.2 g |
| | EPD | 72 g | Pot residue | 124 g (w/A15) |
| | A15 | 3.0 g | TOTAL | 160.2 g |
| | TOTAL | 165 g | | |

TABLE 6

Compositions and species recovery in hydrolysis experiments

| Experiment | Distillate composition (wt %) | | Pot residue composition (wt %) | | Species recovery (%) |
|---|---|---|---|---|---|
| PD Hydrolysis (R11) | BA | 87 wt % | H2O | 69 wt % BA | 97% |
| | H2O | 5.4 wt % | EG | 29 wt % EG | 97% |
| | PD | 2.9 wt % | PD | 0   H2O | 93% |
| | Butyric acid | ~2 wt % | | | |
| EPD Hydrolysis (R12) | BA | 94 wt % | H2O | 65 wt % BA | 99% |
| | H2O | 2.4 wt % | BDO | 33.6 wt % 12BDO | 93% |
| | EPD | 1.4 wt % | EPD | 1.2 wt % H2O | 100% |
| | Butyric acid | ~2.4 wt % | Butyric acid | ~0.2 wt % | |

Note:
Species recovery assumes that PD and EPD are fed pure; butyric acid from BA oxidation.

Acetal Separation

Batch Acetal Separation: The separation of PD from EPD was also successfully demonstrated by operating a packed column at steady state under total reflux. The experimental apparatus consisted of a 250 ml three neck round bottom flask, a distillation column (2.54 cm ID×86.4 cm length packed with stainless steel dumped packing (0.41 cm size; 76.2 cm packing height)), and a condenser. PD (58 g) with a purity of ~95% and EPD (72 g) with purity>98.5% were charged in the round bottom flask. The system was heated to reflux, sampled, and analyzed for component concentrations. The sample from the top of the system included PD:EPD in a ratio of about 90.2:0.07 (w/w), and the sample from the bottom of the system included PD:EPD in a ratio of about 12.6:84.3 (w/w). This system was modeled in ASPENPLUS process simulation software with similar results. This experiment demonstrates the ability to separate the first and second acetalization products 12, 22 according to various embodiments of the disclosure, for example as illustrated in FIG. 1 (column 140) and FIG. 3 (column 340).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PROCESS COMPONENT SUMMARY

10: first polyol reactant (EG)
12: first acetalization product (PD)
20: second polyol reactant (BDO)
22: second acetalization product (EPD)
30: acetalization reactant (BA)
40: water
100, 200, 300, 400: methods for separating polyols
110: reactor (112: feed, 114: outlet)
120: separator (decanter; 124: light or organic phase outlet, 126: dense or aqueous phase outlet)
130: separator (distillation column or evaporator)

140: separator (distillation column; 144: overhead outlet, 146: bottoms outlet)
150: hydrolysis reactor (154: acetalization reactant outlet, 155: separator/decanter, 156: first polyol outlet, 157: separator/distillation)
160: hydrolysis reactor (164: acetalization reactant outlet, 165: separator/decanter, 166: second polyol outlet, 167: separator/distillation)
210: reactor (reactive distillation column; 210A: lower portion of column, 212: feed, 214: overhead outlet, 216: bottoms outlet)
220: hydrolysis reactor (224: acetalization reactant outlet, 225: separator/decanter, 226: first polyol outlet, 227: separator/distillation)
310: reactor (310A, 310B: first and second reactors, 312A,312B: first and second feeds,
314A,314B: first and second outlets)
320: separator (decanter; 320A, 320B: first and second separators, 324A, 324B: first and second light or organic phase outlets, 326A, 326B: dense or aqueous phase outlets)
330: separator (distillation column; 324: overhead outlet, 336: bottoms outlet)
340: separator (distillation column; 344: overhead outlet, 346: bottoms outlet)
360: hydrolysis reactor (364: acetalization reactant outlet, 365: separator/decanter, 366: second polyol outlet, 367: separator/distillation)
410: reactor (reactive extraction column; 410A, 410B: top/bottom of column, 411: polyol feed, 412: acetalization reactant feed, 413: water feed, 414: aqueous phase outlet, 416: organic phase outlet)
420: separator (distillation column; 424: overhead outlet, 426: bottoms outlet)
430: hydrolysis reactor (434: acetalization reactant outlet, 435: separator/decanter, 436: second polyol outlet)
440: separator (distillation column; 424: overhead outlet, 436: bottoms outlet)

What is claimed is:

1. A method for separating polyols, the method comprising:
   feeding to a reactor:
   (i) a first polyol reactant having 2 to 10 carbon atoms and comprising at least two hydroxyl groups on adjacent carbon atoms,
   (ii) a second polyol reactant different from the first polyol reactant, having 2 to 10 carbon atoms, and comprising at least two hydroxyl groups on adjacent carbon atoms,
   (iii) an acetalization reactant comprising at least one of an aldehyde having 1 to 10 carbon atoms and a ketone having 3 to 10 carbon atoms,
   (iv) a first acetalization product comprising a reaction product between the first polyol reactant and the acetalization reactant, and
   (v) optionally water;
   forming in the reactor via an acid-catalyzed reaction:
   (i) optionally further first acetalization product comprising a reaction product between the first polyol reactant and the acetalization reactant,
   (ii) a second acetalization product comprising a reaction product between the second polyol reactant and the acetalization reactant, and
   (iii) water;
   separating a reactor product mixture comprising the first acetalization product, the second acetalization product, the first polyol reactant, and the water into (i) a water-immiscible product comprising the first acetalization product and the second acetalization product, and (ii) an aqueous product comprising the first polyol reactant and the water;
   separating the water-immiscible product into (i) a first product comprising the first acetalization product, and (ii) a second product comprising the second acetalization product; and
   hydrolyzing the second product to form the second polyol reactant from the second acetalization product.

2. The method of claim 1, further comprising:
   recycling the first product comprising the first acetalization product to the reactor.

3. A method for separating polyols, the method comprising:
   feeding to a first reactor:
   (i) a first polyol reactant having 2 to 10 carbon atoms and comprising at least two hydroxyl groups on adjacent carbon atoms,
   (ii) a second polyol reactant different from the first polyol reactant, having 2 to 10 carbon atoms, and comprising at least two hydroxyl groups on adjacent carbon atoms,
   (iii) an acetalization reactant comprising at least one of an aldehyde having 1 to 10 carbon atoms and a ketone having 3 to 10 carbon atoms,
   (iv) a first acetalization product comprising a reaction product between the first polyol reactant and the acetalization reactant, and
   (v) optionally water;
   forming in the first reactor via an acid-catalyzed reaction;
   (i) optionally further first acetalization product comprising a reaction product between the first polyol reactant and the acetalization reactant,
   (ii) a second acetalization product comprising a reaction product between the second polyol reactant and the acetalization reactant, and
   (iii) water;
   separating a first reactor product mixture comprising the first acetalization product, the second acetalization product, the first polyol reactant, and the water into (i) a first water-immiscible product comprising the first acetalization product and the second acetalization product, and (ii) a first aqueous product comprising the first polyol reactant and the water;
   separating the first water-immiscible product into (i) a first product comprising the first acetalization product, and (ii) a second product comprising the second acetalization product; and
   hydrolyzing the second product to form the second polyol reactant from the second acetalization product:
   feeding to a second reactor:
   (i) the first product comprising the first acetalization product,
   (ii) the acetalization reactant, and
   (iii) the aqueous product comprising the first polyol reactant and the water;
   forming in the second reactor via an acid-catalyzed reaction:
   (i) optionally the first acetalization product comprising a reaction product between the first polyol reactant and the acetalization reactant, and
   (ii) the second acetalization product comprising a reaction product between the second polyol reactant and the acetalization reactant;
   separating a second reactor product mixture comprising the first polyol reactant, the second acetalization product, the acetalization reactant, and the water into (i) a second water-immiscible product comprising the second acetalization product and the acetalization reactant, and (ii) a second aqueous product comprising the water; and feeding the second water-immiscible product to the first reactor.

4. The method of claim 1, wherein the first polyol reactant and the second polyol reactant are independently selected from the group consisting of saturated or unsaturated linear hydrocarbon polyols, branched hydrocarbon polyols, and cyclic hydrocarbon polyols.

5. The method of claim 1, wherein the first polyol reactant and the second polyol reactant each have only two hydroxyl groups.

6. The method of claim 1, wherein:
the first polyol reactant is 1,2-ethanediol (ethylene glycol), and
the second polyol reactant is 1,2-propanediol (propylene glycol).

7. The method of claim 1, wherein:
the first polyol reactant is 1,2-ethanediol (ethylene glycol), and
the second polyol reactant is 1,2-butanediol.

8. The method of claim 1, wherein the first polyol reactant and the second polyol reactant are independently selected from the group consisting of 1,2-ethanediol (ethylene glycol), 1,2-propanediol (propylene glycol), 1,2-butanediol, 1,2-butanediol, 2,3-butanediol, 1,2-pentanediol, 2,3-pentanediol, 1,2-hexanediol, 2,3-hexanediol, 3,4-hexanediol, 1,2-heptanediol, 1,2-octanediol, 1,2-nonanediol, and 1,2-decanediol.

9. The method of claim 1, wherein the first polyol reactant and the second polyol reactant have boiling points that are within 10° C. of each other.

10. The method of claim 9 wherein the first acetalization product and the second acetalization product have boiling points that are more than 10° ° C. apart from each other.

11. The method of claim 1, wherein the acetalization reactant comprises at least one of an aldehyde having 3 to 10 carbon atoms and a ketone having 4 to 10 carbon atoms.

12. The method of claim 1, wherein the acetalization reactant is selected from the group consisting of saturated or unsaturated linear hydrocarbon aldehydes or ketones, branched hydrocarbon aldehydes or ketones, and cyclic hydrocarbon ketones.

13. The method of claim 1, wherein the acetalization reactant is selected from the group consisting of propanal, butanal (butyraldehyde), 2-methylpropanal (isobutyraldehyde), pentanal, hexanal, heptanal, octanal, nonanal, decanal, 2-buatanone, 2-pentanone, 3-pentanone, 2-hexanone, 3-hexanone, 2-heptanone, 2-octanone, 2-nonanone, 2-decanone.

14. The method of claim 1, wherein the acetalization reactant comprises butanal (butyraldehyde).

15. The method of claim 1, wherein the acetalization reactant has a solubility in water of up to 30 g/100 ml.

16. The method of claim 1, wherein the first acetalization product and the second acetalization product have a solubility in water of up to 30 g/100 ml.

17. The method of claim 1, wherein the reactor comprises a heterogeneous solid-phase acid catalyst therein for forming at least one of the first acetalization product and the second acetalization product.

18. The method of claim 1, further comprising: feeding to the reactor a homogeneous acid catalyst for forming at least one of the first acetalization product and the second acetalization product.

19. The method of claim 1, further comprising, after forming in the reactor at least one of the first acetalization product and the second acetalization product:
separating a product stream comprising the first polyol reactant and water into (i) a purified first polyol product and (ii) water.

20. The method of claim 1, further comprising, after forming in the reactor at least one of the first acetalization product and the second acetalization product:
separating a product stream comprising the second polyol reactant and water into (i) a purified second polyol product and (ii) water.

21. The method of claim 1, wherein:
conversion of the first polyol reactant to the first acetalization product in the reactor is at most 10%; and
conversion of the second polyol reactant to the second acetalization product in the reactor is at least 70%.

22. The method of claim 1, wherein the reactor is not a reactive distillation column.

23. The method of claim 1, wherein separating a reactor product mixture comprises gravimetrically separating the reactor product mixture into the water-immiscible product and the aqueous product.

* * * * *